United States Patent [19]

Coleman et al.

[11] Patent Number: 4,560,775

[45] Date of Patent: Dec. 24, 1985

[54] PRODUCTION OF LACTONE IN MOLTEN SALT ELECTROLYSIS

[75] Inventors: James P. Coleman; Richard C. Hallcher, both of Maryland Heights; Dudley E. McMackins, St. Charles; Charles R. Penquite, Ballwin, all of Mo.; Steven R. Auvil, Macungie, Pa.

[73] Assignee: Monsanto Company, St. Louis, Mo.

[21] Appl. No.: 503,980

[22] Filed: Jun. 13, 1983

[51] Int. Cl.$^4$ .................... C07D 307/32; C07C 67/05
[52] U.S. Cl. ..................... 549/326; 560/241
[58] Field of Search ................. 549/326; 560/241

[56] References Cited

U.S. PATENT DOCUMENTS

| | | | |
|---|---|---|---|
| 3,927,051 | 12/1975 | de Klein | 260/413 |
| 3,992,417 | 11/1976 | Dessau et al. | 260/343.6 |
| 4,175,089 | 11/1979 | Heiba et al. | 260/343.6 |
| 4,193,886 | 3/1980 | Schoenholz et al. | 252/90 |
| 4,356,317 | 10/1982 | Coleman et al. | 560/241 |
| 4,380,650 | 4/1983 | Coleman et al. | 549/326 |

OTHER PUBLICATIONS

Techniques and Methods of Organic and Organometallic Chemistry, vol. 1, (1969), Edited by Donald B. Denney, pp. 51, 91 and 149, Title Page.

Chemical Engineers' Handbook, John H. Perry, Fourth Edition, Title Page, and pp. 14-1 and 14-2.

Parshall, Catalysis in Molten Salt Media, J. Amer. Chem. Soc., 94, pp. 8716-8719, (1972).

Swain et al, J. Amer. Chem. Soc. 89, pp. 2648-2649, (1167).

Weinberg et al, Tetrahedron Letters, No. 25, pp. 2271-2274, (1971).

Michels and Ubbelohde, J. Chem. Soc. (Perkin Transactions, 1972), pp. 1878-1881.

Primary Examiner—Norma S. Milestone
Attorney, Agent, or Firm—Joseph D. Kennedy; James W. Williams, Jr.

[57] ABSTRACT

Butadiene and acetic acid are reacted with a metal salt oxidant in molten salt medium to form γ-vinyl-γ-butyrolactone. The process includes electrolytic regeneration of the oxidant and provides a simple reaction system which permits product recovery and reactant recycle without extensive solvent handling. A high surface area reactor can be employed.

27 Claims, 4 Drawing Figures

PRODUCTION OF LACTONE IN MOLTEN SALT ELECTROLYSIS

The present invention relates to a process for preparing γ-vinyl-γ-butyrolactone and acetoxyhexenoic acids in which reactants are caused to react in a molten salt medium and the product is separated therefrom. In particular, butadiene and acetic acid are reacted in a molten salt medium containing electrolyte and metal oxidant salts, and the metal oxidant is electrolytically regenerated. The invention also relates to such a process in which the reaction occurs in a reactor having high surface to volume ratio, particularly a packed reactor such as those typified by packed column absorbers, strippers and distillation columns.

BACKGROUND OF THE INVENTION

A commonly assigned U.S. Pat. No. 4,356,317 of Coleman, Hallcher and McMackins, issued Oct. 26, 1982, describes a procedure to react butadiene and acetic acid with metal ion oxidant to prepare acetoxyhexenoic acids. A U.S. Pat. No. 4,175,089 describes a procedure for reacting olefins and acetic acid with metal ion oxidant to produce lactones. The prior procedures are generally conducted in solvents, e.g. in acetic acid, and separation of product generally involves extraction procedures. Particular separation procedures for γ-butyrolactones are described in U.S. Pat. No. 3,992,417. One of the characteristics of prior procedures, particularly those directed to production of acetoxyhexenoic acids, is that initially good selectivity to desired product tends to decline as conversions are increased, or as product concentrations in the reaction mixture are increased. Consequently it may be necessary to operate such processes at economically poor payloads or to develop possibly expensive processing means to retain appropriate selectivity. It has been found that γ-vinyl-γ-butyrolactone is more stable under preparation and isolation conditions than acetoxyhexenoic acids. Procedures for preparing acetoxyhexenoic acids and converting the acids to γ-vinyl-γ-butyrolactone are described and claimed in a simultaneously filed, commonly assigned application of Coleman et al, Ser. No. 503,979. In such procedures with continuous conversion of acetoxyhexenoic acids to γ-vinyl-γ-butyrolactone, it is feasible to keep the acetoxyhexenoic acid content at a low level but operate at a relatively high total payload of acetoxyhexenoic acids plus lactone, with minimal loss of chemical yield and current efficiency. However, such procedures generally require additional equipment with consequent costs and add complexity to the process because of the additional reactions involved. A related commonly assigned application of Coleman and McMackins, simultaneously filed with the present application, Ser. No. 503,982, involves reactions of butadiene and acetic acid with metal oxidant in solvent medium, followed by a separation procedure in which product is separated from molten salt electrolyte.

SUMMARY OF THE INVENTION

The present invention involves reacting butadiene and acetic acid in the presence of metal salt oxidant in molten salt medium. In a particular aspect it involves contacting the molten salt medium at elevated temperature with butadiene and acetic acid in vapor phase and removing γ-vinyl-γ-butyrolactone product by sparging with such reactants. The metal oxidant can be regenerated electrolytically during the reaction process with electrodes in contact with the molten salt medium, or in a separate electrolysis cell through which the molten salts are cycled. The invention effects an efficient removal of product from the reaction medium. It is an object of the invention to avoid undue product degradation by effecting product removal as the reaction proceeds, thereby limiting the product concentration in the reaction medium to relatively low levels. The invention has the advantage of eliminating distillation of large volumes of solvent and handling of solid electrolytes, or utilization of extensive extraction procedures, which have been characteristic of prior processes.

In a particular aspect the invention involves reacting butadiene and acetic acid with a metal oxidant to produce acetoxyhexenoic acids and γ-vinyl-γ-butyrolactone in a reactor with high surface to volume ratio. The reaction system is exemplified by reaction in a packed reactor in which liquid reaction medium containing metal oxidant, acetic acid and salts is contacted by counter current flow of butadiene. The reaction temperature can be sufficiently high to improve reaction rate and to promote the production of γ-vinyl-γ-butyrolactone as product and it is an object to strip the lactone product from the reaction mixture while it is being produced. The contact surface utilized in the present invention is intended to improve absorption of butadiene in liquid reaction medium by improving gas-liquid phase transfer, thereby increasing concentration of butadiene in the liquid reaction medium and its availability for reaction. The stripping of product from the reaction medium may also be facilitated, and in general reaction rate and attainment of equilibrium conditions will be promoted. As in prior procedures, it may be advantageous to utilize acetic anhydride as a reaction component along with acetic acid. The amount of acetic acid and acetic anhydride in the reaction medium will be affected by the reaction temperature and butadiene vapor stream, and at the fairly high temperatures contemplated, the acetic acid and acetic anhydride levels may be such that the reaction medium can be considered a molten salt medium rather than salts dissolved in solvents. The reaction medium can involve electrolyte salts along with metal oxidant salts, and salts will generally be selected to have melt properties such as to make the reaction medium liquid under reaction conditions. Alkali metal acetates can be used as electrolyte salts, and inclusion of lithium acetates can contribute to lower melting characteristics.

DETAILED DESCRIPTION

The present invention provides a simple procedure for effecting the desired reaction in a molten salt medium and quickly removing product. A reactant stream is passed through the molten salts, reacting to some extent as it contacts the salts, and with product being removed in the reactant stream. Butadiene and acetic acid are the essential reactants and generally constitute the reactant stream. A 50% by weight solution of butadiene in acetic acid (prepared under pressure) can, for example, be used. The acetic acid reactant, being less volatile than butadiene, can constitute a fair proportion of the salt reaction medium. However, if supplied as an original component, it will still have to be replaced to the extent it is removed with product, in order to maintain desired concentration for the reaction. The metal salt oxidant for the reaction, along with electrolyte salts, will generally constitute the molten salt medium. Manganese III ion is the preferred metal oxidant for use, and will generally be used for illustration herein. Vanadium and cerium are examples of other metals which can be used in suitable elevated valence states. In addition to the main metal oxidant, an additional metal oxidant, particularly cupric ion, can be used for additional effect. When utilized, copper salts will ordinarily be provided as part of the salt medium.

The reaction of butadiene and acetic acid with metal salt oxidant can lead to γ-vinyl-γ-butyrolactone, acetoxyhexenoic acids, or both as products. Also the acetoxyhexenoic acids may be converted to the lactone, and there is some advantage in effecting this conversion in order to have a more stable compound for separation, as described and claimed in a simultaneously filed, commonly assigned copending application of Coleman et al, Ser. No. 503,979. In the present process both acetoxyhexenoic acids and γ-vinyl-γ-butyrolactone can be produced and removed as product. Both are useful products, being convertible to sorbic acid. The proportions of the products will vary with reaction conditions, particularly with the presence of acetic anhydride in the reaction mixture. Acetic anhydride has an influence in improving reaction rate and directing the reaction toward production of acetoxyhexenoic acids. Some acetic anhydride will ordinarily be provided to the reaction medium in order to remove water present as salt hydrates. Additional amounts of acetic anhydride can be provided to the extent useful in contributing to selectivity to desired reaction products. Results indicate that some acetic anhydride is useful in improving selectivity based on combined production of acetoxyhexenoic acids and γ-vinyl-γ-butyrolactone as desirable products.

As stated, it is feasible to cycle the butadiene and acetic acid through the molten salt reaction medium. In an alternate procedure, the acetic acid can be present as a substantial part of the reaction medium, and such acetic acid can serve as a reactant, while product is removed by a butadiene stream. The extent to which the acetic acid remains in the reaction stage will depend upon reaction temperature and the extent to which reflux condensers or other means are used. Similarly it is feasible to maintain butadiene in contact with the salt in a reaction vessel rather than cycling the butadiene through the reaction vessel, using pressure vessels if desired. However, cycling the butadiene is adapted to procedures for continuous product separation. The amount of acetic acid present as part of the molten salt mixture can vary widely, as it is not an essential component other than having to be present as a reactant and to have appreciable contact time with the oxidant salt and butadiene at elevated temperature. However, the amounts of acetic acid will generally be in the range of about 20% to about 50% by weight of the molten salt mixture.

For illustration of apparatus for effecting the invention,

FIGS. 1, 2 3 and 4 are provided.

Figure 1:
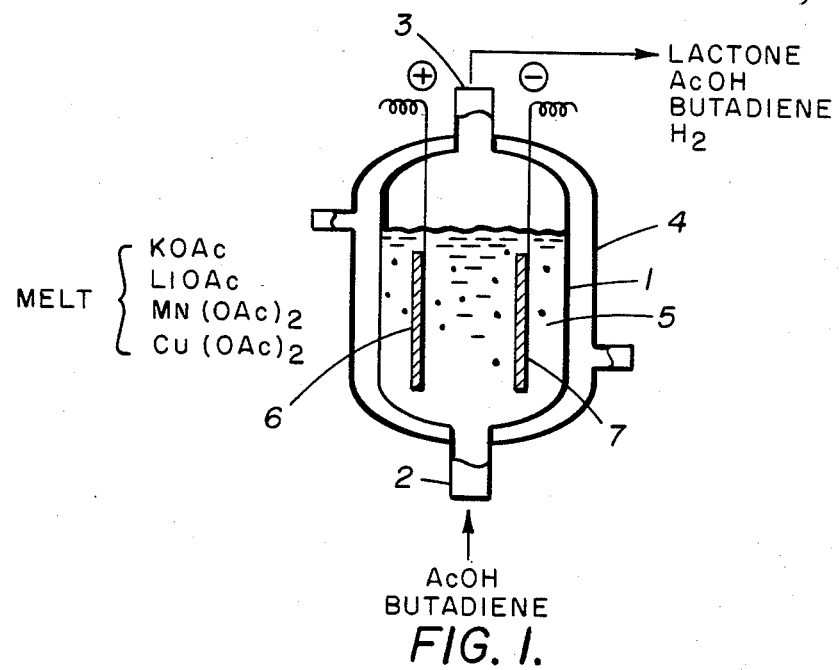
FIG. 1 is an illustration of a reactor-cell with electrodes and molten salt reaction medium.

The acetoxyhexenoic acids produced in the present process are a combination of 4-acetoxy-5-hexenoic acid and 6-acetoxy-4-hexenoic acids. Some other isomers may be present, but these are the predominant isomers and generally constitute substantially all of such acids present. Some anhydride forms of the acids may at times be present.

In processes conducted in solvent solutions, particularly those directed to production of acetoxyhexenoic acids, copper II salts were found useful in improving selectivity, presumably by facilitating oxidation of an acetic acid butadiene radical intermediate before it reacted with additional butadiene. The copper salts may serve a similar purpose in the present process, as slightly better selectivities may be obtainable with proper concentrations of such salts present. However, use of copper salts is not required, and under the conditions of the present process copper ions can cause the production of acetoxyacetic acid, presumably by causing oxidation of an acetic acid radical intermediate. If copper ions are used, the amounts will preferably be small in order to avoid undue production of acetoxyacetic acid. The amounts of copper salts may, for example, constitute less than 0.5% by weight of the molten salt medium, and may generally be in the range of 0.02% to 0.1% by weight of the medium. Amounts of acetic anhydride can be varied, depending upon acceptability of acetoxyhexenoic acids as a major product and contemplated further conversion or separation procedures. If used at all (in excess of that to take up water of hydration), it may be used in relatively high amounts up to 80 or more mole per 100 moles of acetic acid, but the most advantageous use may be in range of 4 to 10 or 15 moles per 100 moles of acetic acid.

The salts utilized in the present invention are such as to remain molten or at least fluidized at the temperature at which the reaction is effective and product is removed from the reaction mixture. The salts are chosen so as to have requisite melting characteristics, as in a particular example including lithium acetate along with potassium or other alkali metal acetates, in order to lower the melting point of the latter. Inorganic and organic salts can both be used if possessed of suitable melting characteristics, although many inorganic salts are too high melting to be of interest. The product separations involved will usually be accomplished at temperatures no greater than about 175° C., so it is desirable to employ salt compositions which are substantially liquid at that temperature, or at even lower temperatures if lower operating temperatures are selected. In any event, the salt composition should be in a substantially liquid or fluid state at the chosen temperature, which preferably will not be over about 160° C., and which often will be 150° C. or less, such as 130°–135° C. It may be convenient to employ salts which are liquid at somewhat lower temperatures than those employed, such as around 100° C., or so, to allow for some cooling without solidification in material transfer procedures, such as in pumping the salts to a mix tank, or back to a reaction vessel. Of course, if necessary, heating means can be employed to maintain a suitable temperature during such operations.

The melting points of salts can be used as a guide in selection of salts for use herein. However, because of the usual presence of both metal oxidant and electrolyte salts in the present process, melting point-lowering effects of mixtures are involved, and a particular mixture with suitably low melting characteristics can be employed even if some components have melting points which are higher than those operating temperatures. If desired, eutectic mixtures of salts can be employed, but other salt mixtures of sufficiently low melting characteristics can be employed.

As indicated above, lithium salts are useful in lowering the melting point of alkali metal salt mixtures, particularly alkali metal acetates. In the reactions exemplified herein, a metal oxidant is employed, preferably a manganese compound, although cesium and vanadium compounds can also be used. Also, it is generally preferred to use copper compounds in conjunction with the manganese compound. Thus the salt compositions in the present process usually include manganese (or other metal oxidant) and copper salts along with electrolyte salts. Alkali-metal salts are convenient for use as electrolyte to improve conductivity, although other supporting electrolytes can be used. Manganese and copper salts contribute to conductivity, but it is desirable to have other electrolyte salts present. Sufficient manganese salt will be used to provide metal oxidant needed. Much larger amounts can be used, but the salt mixtures of suitable melting characteristics will be selected. Ordinarily the manganese salts will constitute about 10% to about 50% by weight of the salts, but higher or lower amounts can be used. Amounts from 25% to 35% by weight are convenient for use. Such amounts of manganese acetates can, for example, suitably be employed with an alkali metal acetate mixture which has lithium acetates in slight molar excess over other alkali metal acetates.

Since the reactions exemplified herein involve reactions of acetic acid (directly or indirectly), it is convenient to use acetate salts as electrolytes in the process. An excess of acetic acid is also generally present. The use of acetate salts avoids possible complication of separation or other procedures by unnecessary presence of extraneous ions. Potassium or sodium acetates can be used suitably in conjunction with lithium acetates, and such combinations can be employed with the usual ranges of manganese and copper salts. The manganese and copper compounds can also be considered as acetates in the usual acetic acid environment, regardless of the form in which added to the reaction mixture.

With acetate salts, lithium is particularly useful as a cation to lower melting points, but ammonium acetates can also be used, including that of the ammonium ion, as well as mono-, di- or tri-substituted or quaternary ammonium ions. Particular salts of cations other than lithium will have suitably low melting points, such as particular salts of carboxylic acids, such as of medium to higher molecular weight carboxylic acids, or, with some cations, the halide or thiocyanate salts can suitably be employed. In the case of ammonium, substituted ammonium and quaternary ammonium cations, a number of anions provide salts of suitably low melting point.

In the procedures herein, a salt medium is utilized which is primarily composed of the metal oxidant and electrolyte salts. However, complete separation of product will not ordinarily be obtained and the salt residue will have some residual product present, such as small, minor amounts of γ-vinyl-γ-butyrolactone or acetoxyhexenoic acids. Such materials, along with the generally larger amounts of acetic acid present, have some tendency to liquefy the salts at temperatures lower than would be required otherwise, and this can be taken into consideration when selecting salts for suitable properties. The present invention generally contemplates continuous procedures in which reactants and product will continuously be present. However, even for batch operation, during and prior to completion of distillation, of course, the salts will necessarily be accompanied by the product or other material being distilled, which will have some tendency toward liquefying the salt composition. It is likely that even some small amount of acetic acid is still present in the salts, in a form analogous to water of hydration, after the bulk of the desired product has been distilled. Even such small amounts of acetic acid are apt to have some effect in lowering the melting point of the salts.

In carrying out the present invention, reaction conditions in general can be employed which are suitable for preparation of acetoxyhexenoic acids or γ-vinyl-γ-butyrolactone, but with use of salts in the reaction mixture which have low melting point characteristics as described herein. Thus, manganese and copper compounds can be utilized in the usual manner, along with an electrolyte salt such as potassium acetate. A sufficiently low melting point can then be assured by inclusion of lithium acetate, either as replacement for all or part of the usual amount of potassium acetate, or in addition thereto. Lithium acetate dihydrate can be used as the sole electrolyte salt if desired. However, cost or other considerations may make it desirable to use lithium acetate along with potassium acetate, with potassium being present on a mol basis in up to a 7:1 ratio to lithium, preferably from about 1:1 up to about 5:1 mol ratio of potassium to lithium. Similar proportions can be used with mixtures of lithium and sodium acetates, although sodium acetate itself is somewhat higher in melting point than potassium acetate. The actual melting characteristics of compositions are influenced by type of composition, such as solid solution, congruent compound, and whether an eutectic composition is formed, and in the present instance by the presence of minor amounts of manganese and copper salts along with those of other cations, such as lithium and other alkali metals. Mixtures of several electrolyte salts can also be used, e.g. mixtures of sodium, potassium and lithium acetates, and in some cases having a third component may contribute to lower melting characteristics. Various ammonium ions may be used, with ammonium acetate itself having a fairly low melting point. Quaternary ammonium salts for the most part have relatively low melting points, and in particular, quaternary ammonium salts, such as tetrabutyl ammonium salts, or salts of other tetralkyl ammonium ions with alkyl groups of at least 4 carbon atoms, tend to have low melting points, with this being true for the chloride, bromide, iodide, acetate, etc. salts.

Quaternary ammonium salts of various carboxylic acids can be used. Suitable low melting electrolyte salts, can, for example, be composed of mixtures of low melting quaternary ammonium salts, particularly those with substituents on the nitrogen atom having at least four carbon atoms, with one or more alkali metal salts. For example, such quaternary ammonium salts, particularly acetate salts, may be used in admixture with potassium acetate; if desired, lithium acetate can also be included to obtain the effects of both the lithium and quaternary ammonium salts on the melting characteristics. It will be recognized that there will be considerable variation in the melting characteristics of various salt compositions, but one can readily determine whether particular mixtures have suitable melting characteristics for particular operating conditions.

In addition to melting characteristics, the electrolyte salt selected should have suitable properties as an electrolyte and should not unduly interfere with the desired reactions. Salts with anions such as sulfonates, e.g. toluenesulfonate, or phosphonates are not likely to interfere, and the quaternary ammonium salts with such anions, particularly with tetrabutylammonium or other quaternary ammonium cations described above, are likely to have low melting characteristics. Quaternary ammonium benzoate salts also tend to be low melting, particularly tetrahexylammonium benzoate which is a liquid at room temperature and is unlikely to interfere in electrolysis by discharge at the electrodes. Acetate salts are particularly suitable as acetates and acetic acid are involved in the desired reactions, and acetates have been demonstrated to be useful supporting electrolytes to carry the electric current. However, salts with other anions give good conductivity and carry electric current, and can be employed herein, although consideration should be given to effectiveness compared to the acetate, and potential interference in the chemical reactions or by unwanted discharge at the anode.

In the product separations herein, it will generally be advantageous to remove product in lactone form, as γ-vinyl-γ-butyrolactone can be more readily distilled than can its related acetoxyhexenoic acids. The γ-vinyl-γ-butyrolactone can be distilled at approximately 150° C. at 90 mm, Hq., while a mixture of 4-acetoxy-5-hexenoic and 6-acetoxy-4-hexenoic acids require a pressure less than about 0.1 mmHg for distillation at 130°–150° C. Thus the acetoxyhexenoic acids can be separated by distillation in accord with the present invention, although practical considerations weigh against such procedure for large scale use. The γ-vinyl-γ-butyrolactone has a boiling point of 220° C. A mixture of acetoxyhexenoic acids was found to give 88% purity 4-acetoxy-5-hexenoic acid at 98°–102° C. 0.05 mmHg and 95% purity 6-acetoxy-4-hexenoic acid at 110°–114° C./0.05 mmHg. It has been found that a mixture of butadiene and acetic acid sparged into a molten salt mix with 6% by weight γ-vinyl-γ-butyrolactone content, is capable of producing an acetic acid concentrate with 1.8 mole percent content of the lactone. It is contemplated that the lactone process can be conducted with less than 10 or so weight percent lactone in the reaction medium with continuous removal by a butadiene and acetic acid stream. The addition rate of the reactants can be adjusted in conjunction with the reaction temperature, possibly in the 130°–150° C. range, to obtain steady state conditions at low lactone content to avoid undue product degradation. Lower temperatures can be used to the extent a liquid medium is achieved. Higher temperatures up to 180° C. or higher permit better product removal but may give poorer selectivity to desired product.

FIG. 1 is an illustration of a simple reaction and electrolysis cell. The vessel 1 has inlet 2 for reactants and outlet 3 for product and other reaction components. The vessel is equipped with a heating jacket 4 for circulation of heating fluid. The vessel contains a molten salt bath 5 as reaction medium in which cathode 6 and anode 7 are suspended and connected by wires to positive and negative current sources respectively. In operation acetic acid and butadiene are admitted through inlet 2 to contact the hot salt bath 5 and product and reactants exit through outlet 3 to a condenser, distillation unit or other means for separation and collection of product, γ-vinyl-γ-butyrolactone and acetoxyhexenoic acids, and recycle of the reactants to inlet 2. The cell is illustrated without a divider and can be operated in this mode, but a divider can be employed if desired.

Figure 2:
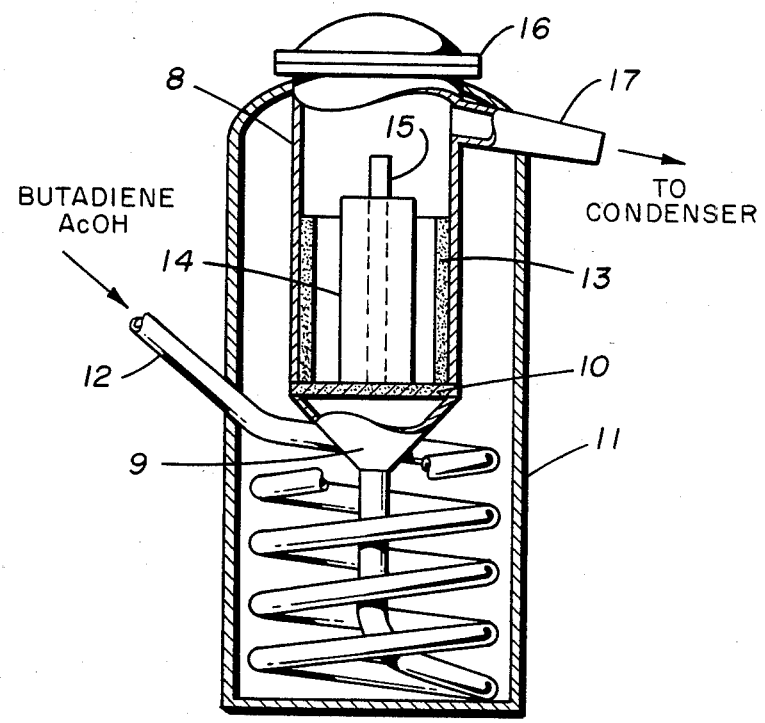
FIG. 2 illustrates a particular reactor-cell with separate cathode compartment.

FIG. 2 illustrates a reactor cell in which a glass cylinder 8 is employed as a reaction vessel. The cylinder has a bottom 10 which is a porous glass filter frit. The cylinder is supported on a funnel 9. The cylinder and funnel are within a heating jacket 11 provided with a conduit 12 in the form of vaporization coils connected to the bottom of funnel 9. The cylinder 8 has a cylindrical graphite felt anode 13 and an alundum cup cathode compartment 14 containing a cathode 15 such as a graphite rod or metal foil or wire. The cylinder 8 has a lid 16 and an outlet 17 to a condenser or other product separation and collection means. In operation the cylinder 8 is provided with a salt mixture as described herein which is heated by the oil bath in the oil jacket to form a melt supported on glass filter frit 10. Liquified butadiene and acetic acid are admitted to conduit 12 and vaporized by passage through the conduit coils, and pass through funnel 9 and glass frit 10. The flow rate can be adjusted so that the salt melt is supported on the glass frit and mixed by the upflow of gas. The gases with some entrained product then exit through outlet 17, If desired, the reactor cell can be operated as an undivided cell, in which case alundum cup cathode compartment 14 will not be present. The butadiene and acetic acid may be conveniently used as a 50% weight mixture of butadiene in acetic acid, but other mixtures can be used, from say 20% to 80% butadiene. Moreover, the butadiene can be added separately from the acetic acid.

EXAMPLE 1

A reaction was carried out in the gas-sparged electrolysis cell of FIG. 2. The cell was equipped with a distillation condenser to condense the product stream. To prepare anolyte, a solution was formed of the following (wherein Ac stands for acetyl):

30 g—$Mn(OAc)_2.4H_2O$
30 g—$Li(OAc).2H_2O$
40 g—KOAc
125 ml—$Ac_2O$
350 ml—HOAc

The solution was stripped at 40° C. and 15 mm Hg pressure, and then charged to the cell heated to 150° C. A catholyte was prepared by similarly stripping a solution of the following:

15 g—KOAc
15 g—$LiOAc.2H_2O$
30 ml—$Ac_2O$
100 ml—HOAc

The catholyte was charged to the alundum cup of the cell and a liquid solution (under pressure) of 50%, 1,3-butadiene in acetic acid was admitted at a rate to provide good mixing of the anolyte salt melt by the upward flow of gases. After an equilibration period, current was applied at 0.75 ampere for 2.5 hours. Analysis showed current efficiency of 58% to γ-vinyl-γ-butyrolactone and 2% to acetoxyhexenoic acids. The cell was modified by removing the alundum cup and a small zirconium wire was used as the cathode in the undivided cell. Reaction at 150° C. gave approximately 50% current efficiency, mainly to the lactone with a small amount of acetoxyhexenoic acids. Approximately one-half of the lactone product was swept out of the salt under these conditions and found in the product condensate. Similar results were obtaned with an undivided cell with a graphite cathode.

A modification of the procedure, using 135° C. and 0.2 ampere current for 1.0 ampere hour, in a divided cell with a wire cathode, gave about 85% current efficiency to γ-vinyl-γ-butyrolactone and about 2% to acetoxyhexenoic acids, with 26% of the lactone being carried out to product condensate. A similar procedure with 1.2% acetic anhydride in the feed gas gave about 80% current efficiency to the lactone and about 15% to acetoxyhexenoic acids.

When a procedure was employed with a divided cell in accord with Example 1, but with a fairly high amount of copper present, 8 g Cu(OAc)$_2$.H$_2$O, the product at 150° C. was acetoxy acetic acid. Similar results were obtained at 130° C. but some acetoxyhexenoic acids were produced.

In the above procedures, the acetoxy hexenoic acids are primarily a mixture of 4-acetoxy-5-hexenoic acid and 6-acetoxy-4-hexenoic acid. The acetic anhydride employed in the electrolyte preparations is intended to take up water of hydration, rather than be present as a reactant.

EXAMPLE 2

The reaction system of Example 1 was modified to provide for recycle of acetic acid, partly to obtain more concentrated product condensate for analysis. The conduit from the cell had a water-cooled distillation column condensing acetic acid and product, but permitting venting of butadiene and hydrogen. The condensate was collected in a reboiler from which acetic acid was distilled through a column and condenser, and the condensed acetic acid recycled by a pump to the electrolysis cell. A reaction employing an undivided cell similar to those in Example 1 gave 56% current efficiency to γ-vinyl-γ-butyrolactone with a small amount of acetoxyhexenoic acids.

EXAMPLE 3

The electrolysis cell utilized in Example 1 was modified so as to have a reflux condenser overhead rather than a distillation condenser. A reaction was conducted with acetic acid and butadiene in molten salts at 135° C., but employing substantial amounts of acetic anhydride and cupric acetate as additional components. Initial current efficiency was good, approaching 90% overall current efficiency (γ-vinyl-γ-butyrolactone and acetoxyhexenoic acids) with about 35% current efficiency to γ-vinyl-γ-butyrolactone. This current efficiency measured when total product concentration (calculated as lactone) in the melt was slightly over 1% by weight, declined to less than 40% overall current efficiency at a product concentration near 5%.

The salt mixture employed in the foregoing example utilized a "standard" mixture obtained by dissolving lithium acetate (60 g), potassium acetate (80 g) and Mn(OAc)$_2$.4H$_2$O (60 g) in acetic acid (400 cc) plus acetic anhydride (222 g) at 70° C. Solvent was stripped off, and the residue redissolved in a minimal amount of acetic acid and stripped again (to remove excess acetic anhydride). The weight of the residue was then brought up to 333 g by the addition of acetic acid. The mixture then had an acetic acid content approximating 40% by weight. For the salt melt in the foregoing example, a 175 gram amount of the standard mixture was used along with 10 grams acetic anhydride and 0.16 gram copper (II) acetate.

EXAMPLE 4

The procedure of Example 3 was employed, but with a salt mixture composed of 82.5 grams of the standard salt mixture as described for Example 3, 50 grams tetrabutylammonium acetate, 33 grams acetic acid and 0.2 grams copper (II) acetate. The ammonium salt was employed to improve solubility of the butadiene; butadiene solubility improves from about 11 mmol/l in the standard mixture to 35 mmol/l at 135° C. in a mixture containing 30% by weight tetrabutylammonium acetate. Electrolysis at 135° C. gave overall current efficiency in the range of about 90 to 80% as total product increased from about 0.5% to 1.5%. The current efficiency to γ-vinyl-γ-butyrolactone was in the range of about 50 to 60% throughout the run.

EXAMPLE 5

A procedure similar to Example 3 was effected. The salt melt used in Example 3 was used, but with 10 grams acetic anhydride as an additional component. The initial current efficiency was very good, being an overall efficiency in the range of 90 to 100 until the product content reached 2% by weight. Most of the product was acetoxyhexenoic acids with only a small amount of lactone being produced. The overall current efficiency declined with continued reaction, being less than 60% when the product concentration reached 3.5%.

EXAMPLE 6

Figure 3:
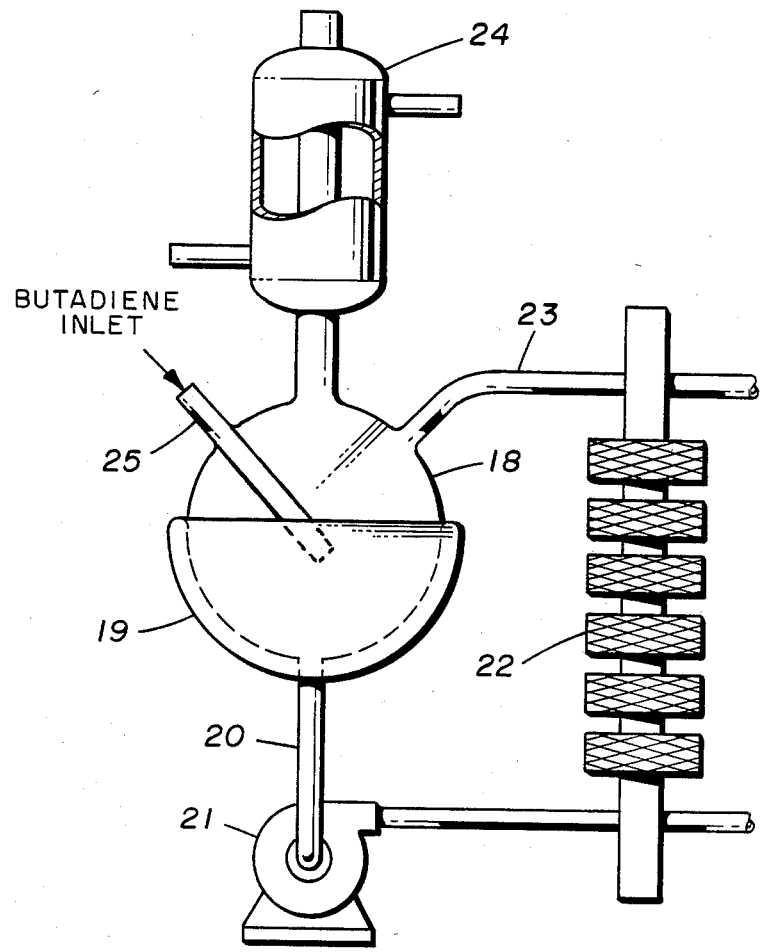
FIG. 3 illustrates a system with separate reaction vessel and electrolysis cell.

A reaction system was used which included a reaction vessel for reaction in a salt medium, and a separate electrolysis cell for regeneration of the manganic ion, as illustrated in FIG. 3. The reaction vessel 18 was a flask, in a heated reservoir, 19 with an outlet 20 from the bottom of the flask for cycling the reaction medium by pump 21 through heated electrolysis cell 22 and back to an inlet 23 to the reaction vessel. The reaction vessel was equipped with a water-cooled condenser 24 (coil) to prevent loss of acetic acid.

Butadiene was admitted to the reaction vessel through an inlet tube 25 to contact the salt medium which is in the vessel 18. Unreacted butadiene was permitted to escape through the condenser 24. The electrolysis cell of which details are not illustrated, was a plate and frame cell with membrane divider. The anode was a graphite felt bonded to a graphite plate. The divider was a Nafion ®425 fluoropolymer resin membrane, being composed of fluorinated hydrocarbon resin with pendant ether groups having sulfonic acid substituents. The cathode was stainless steel. Turbulence promoters and spacers to space the membrane from the electrodes were utilized, in general as described in the aforesaid U.S. Pat. No. 4,356,317. Ryton ® polyphenylene sulfide resin material was used for spacers and cell material in order to have material relatively unaffected by the temperatures used. The anode was effectively masked by the turbulence promoters to leave approximately 16 cm$^2$ of operative area. Anolyte flow rate was approximately 2 liters/minute. While details of the cell and its operation are provided for illustration, these can be varied greatly, especially as described in the aforesaid U.S. Pat. No. 4,356,317. A reaction was conducted using 294.1 grams of the standard salt mixture described above with respect to Example 3, to which 0.26 gram copper(II) acetate and 16.6 grams acetic anhydride were added. Reaction was conducted at a temperature of 135° C. and 0.8 ampere current for slightly over 8 hours. Results are reported in Table 1, showing the current efficiency to lactone, acetoxyhexenoic acids and total product, along with the total product weight percent (calculated lactone)

TABLE 1

| Sample | % Current Efficiency | | | Wt. % Conc. Total Product (as lactone) |
|---|---|---|---|---|
| | Lactone | Acetoxy hexenoic acids | Total | |
| 1 | 16 | 75 | 91 | 0.99 |
| 2 | 18 | 67 | 85 | 1.89 |
| 3 | 21 | 60 | 81 | 2.74 |
| Final | 19 | 56 | 75 | 3.5 |

The procedure employing low levels of copper and acetic anhydride favored acetoxyhexenoic acids with the γ-vinyl-γ-butyrolactone as a minor product, and the initial good current efficiency declined as the weight concentration of product in the reaction medium increased.

EXAMPLE 7

A reaction similar to that in Example 6 was conducted, employing 232.8 grams of the above-referenced standard salt mixture with 14 grams anhydride and 0.2 gram copper (II) acetate. Results are reported in Table 2.

TABLE 2

| Sample | % Current Efficiency | | | Wt. % Conc. Total Prod. (as lactone) |
|---|---|---|---|---|
| | Lactone | Acetoxy hexenoic acids | Total | |
| 1 | 11 | 80 | 91 | 1.08 |
| 2 | 12 | 70 | 82 | 2.32 |
| 3 | 13 | 89 | 72 | 3/09 |
| 4 | 12 | 54 | 66 | 3.72 |
| 5 | 12 | 53 | 65 | 3.53 |
| F | 15 | 48 | 63 | |

A reaction was conducted using 256 grams of the above-referenced standard salt mixture, with no copper salt or added anhydride. The current was 0.8 ampere at 136° C. for approximately 10.5 hours. Results are reported in Table 3.

TABLE 3

| Sample | % Current Efficiency | | | Wt. % Conc. Total Prod. (as lactone) |
|---|---|---|---|---|
| | Lactone | Acetoxy hexenoic acids | Total | |
| 1 | 56 | Not detected | — | — |
| 2 | 56 | 13 | 69 | 1.62 |
| 3 | 53 | 13 | 66 | 2.48 |
| 4 | 46 | 13 | 59 | 3.12 |
| F | 43 | 13 | 56 | 3.85 |

The γ-vinyl-γ-butyrolactone is now the major product, but total current efficiency is lower than in Examples 5 and 6.

EXAMPLE 8

A reaction was conducted using a fair amount of copper (II) acetate, but no added acetic anhydride. The reaction medium was 291 grams of the above-referenced standard salt mixture and 0.36 gram copper (II) acetate. Results are reported in Table 4.

TABLE 4

| Sample | % Current Efficiency | | | | Wt. % Conc. Total Prod. (as lactone) |
|---|---|---|---|---|---|
| | Lactone | Acetoxy hexenoic acids | Acetoxy acetic acid | Total | |
| 1 | 45 | 10 | 14 | 69 | 0.80 |
| 2 | 45 | 11 | 14 | 70 | 1.63 |
| 3 | 43 | 10 | 13 | 66 | 1.85 |
| 4 | 40 | 11 | 13 | 64 | 2.28 |
| 5 | 35 | 12 | 11 | 58 | 2.86 |
| F | 34 | 12 | 11 | 57 | 3.26 |

As indicated in Table 4, the reaction produced a small amount of acetoxy acetic acid, along with the other products.

EXAMPLE 9

A reaction was conducted as in Example 6, using a 0.8 ampere current at 135° for 10 hours. Results are reported in Table 5.

TABLE 5

| Sample | % Current Efficiency | | | Wt. % Conc. Total Prod. (as lactone) |
|---|---|---|---|---|
| | Lactone | Acetoxy hexenoic acids | Total | |
| — | — | — | — | — |
| 2 | 10 | 65 | 75 | 1.04 |
| 3 | 8 | 48 | 56 | 1.52 |
| 4 | 10 | 44 | 54 | 2.21 |
| 5 | 11 | 39 | 50 | 2.88 |
| F | 10 | 37 | 47 | 3.03 |

In the above procedures involving recycle of the salt medium with continuous addition of butadiene to the reaction vessel, the acetic acid present in the salt melt medium was sufficient to provide acetic acid reactant and the acetic acid concentration did not change greatly during the time the reaction was continued. For long term continuous reactions, additional acetic acid can be added to the reaction vessel, on an intermittent or continuous basis, along with the butadiene or by separate addition.

While illustrations herein demonstrate feasibility of the invention many variations from the illustrated procedures are possible and may give improved results. Positive and negative factors of various promoters can be taken into consideration. Thus higher temperatures tend to promote faster reaction and better product removal from the reaction medium, but may also affect product degradation and selectivity to desired product. Also, solubility of the butadiene in the reaction medium declines with increasing temperature. The rate at which butadiene and acetic acid are cycled through the reaction medium affects the concentrations of these components in the reaction medium, as well as the rate of removal of the product. In practice it will be desirable to regulate the various factors to obtain the best balance of acceptable reaction rate and selectivity to desired product with efficient use of equipment, without excessive materials handling because reactant circulation rates or the extent of recycling.

Figure 4:
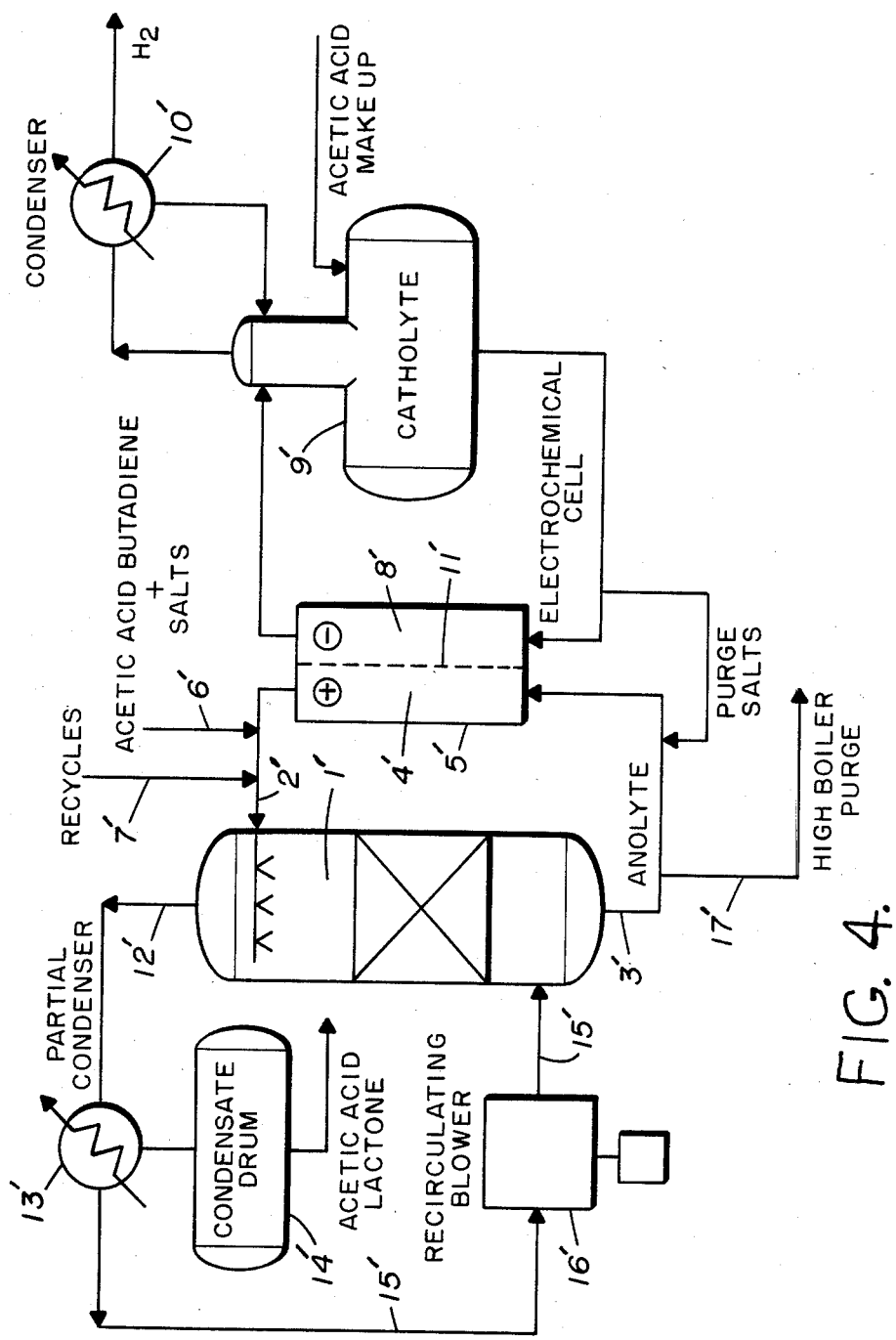
FIG. 4 illustrates a reaction system with high contact surface. The Figures are described in more detail hereinbelow.

FIG. 4 illustrates a reaction system with a high surface reactor. In the system 1' is a packed reactor to which reactants are admitted by line 2' and discharged by line 3' which leads to the anolyte chamber 4' of electrolysis cell 5'. The materials admitted to packed reactor 1' by line 2' include recycle from the electrolysis cell, as well as new reactants and salts from line 6' and possibly recycle material from product separation from line 7'. There is also provision for circulation of catholyte from catholyte chamber 8' through catholyte reservoir 9', and a condenser 10' through which hydrogen is vented. As illustrated, the system uses a divided cell with membrane 11', and a catholyte circulation system, although it is feasible to use an undivided cell and to cycle all electrolyte between the reactor and electrolysis cell. The reactor 1' also has provision for discharge gas or vapors overhead through line 12' to partial condenser 13' from which acetic acid and lactone are collected in condensate drum 14', from which acetic acid and lactone can be discharged for separation by distillation. Acetic acid can be recycled to the reactor. The more volatile materials from partial condenser 13', mainly butadiene with some acetic acid, are recycled by line 15' through recirculating blower 16' to the lower portion of packed reactor 1'. In operation liquid reaction medium containing salts and some acetic acid will be admitted by line 2' to trickle down through the packing in packed reactor 1' while butadiene admitted by line 15' is flowing counter-current to the reaction medium containing acetic acid. The reactor 1' is a packed reactor tower which contains inert packing designed to give high surface to volume ratio, such as used in absorption or stripper columns. The vapors leaving condenser 13' can be compressed and recycled by line 15'. The reactor bottoms discharge line 3' has provision for purge of high boiler materials by line 17'. The packed reactor 1' will be provided with heating means (not illustrated) for effective heating and heat transfer to obtain and maintain desired elevated temperatures in the tower and to transfer heat to reactants and reaction medium to heat such materials to desired reaction temperatures. Usual means for such heating in absorption, distillation or reaction columns can be employed along with thermocouples and other measuring and control devices for controlling the temperatures. Appropriate heating and cooling means can be employed elsewhere in the system for preheating, condensation and the like as needed.

One of the purposes of the high surface area contact system is to facilitate rapid reaction with prompt removal of product. The packed reactor 1' is intended to provide good contact and mixing of reactants at reaction temperature, which may be higher than usually employed in other systems. The main product produced in the present invention is intended to be $\gamma$-vinyl-$\gamma$-butyrolactone, which can be entrained with cycling reactant, and removed from the packed reactor. In the reaction involved, acetoxyhexenoic acids can be produced along with $\gamma$-vinyl-$\gamma$-butyrolactone. The acetoxyhexenoic acids are substantially all composed of 4-acetoxy-5-hexenoic acid and 6-acetoxy-4-hexenoic acid, although presence of minor amounts of other isomers is possible.

In addition to temperature, the ratio of lactone and acetoxyhexenoic acids produced in a high surface area reactor will be influenced by acetic anhydride reactant. Acetic anhydride tends to improve reaction rate and to direct the reaction toward acetoxyhexenoic acids. Under some conditions acetic anhydride improves selectivity to desired product, considering combined production of $\gamma$-vinyl-$\gamma$-butyrolactone and acetoxyhexenoic acids. Since $\gamma$-vinyl-$\gamma$-butyrolactone is the better product for product removal, the amount of acetic anhydride employed in a high surface reactor will be regulated for a proper balance of reaction rate and selectivity with suitable production of lactone for removal.

In the reaction, higher reaction temperatures promote the production of lactone rather than acetoxyhexenoic acids. However the temperature also affects solubility of reactants in the reaction medium, and the extent of product degradation.

A high surface area reactor for use herein is an apparatus for contacting a liquid and gas (or vapor) stream continuously, such as the type of columns commonly used for absorption, stripping or desorption, or distillation. In general apparatus designed for such unit operations can be employed as the high surface area contact reactor in the present invention. The reactor can be a tower filled with irregular solid packing material. Ordinarily, a packed column will be used when employing a high surface area reactor herein, although plate or other types of absorption tower can be employed. The packed column generally includes a cylindrical shell containing a support plate and redistributor plates supporting the packing. A liquid distributor is set above the packing and designed to provide effective irrigation of the packing. Many packing materials are commercially available. The packing materials can be of various geometries, such as Raschig rings, Berl saddles, Lessing rings, Intalox saddles, Pall rings, etc., and can be of various materials, with a preference for material which is inert, such as ceramics, plastics, carbon, glass, or various non-corrosive metals. The pieces of packing material can be of the usual dimensions, generally in the range of $\frac{1}{2}$ inch to 2 inches (1.27 to 5.08 cm) or so, such as 1 to 2 inch (2.54 to 5.08 cm) ceramic or carbon rings, or 1 inch (2.54 cm) saddles. The tower is intended to provide good mass transfer between gas and liquid phases, and also good diffusion in the phases. The tower can vary in height but will preferably be of sufficient height to provide good contact and mixing of the phases. However it will be undesirable to have the height such as to prolong contact and to delay removal of product unnecessarily. Ordinarily the tower will be at least near a meter in height, and the preferred height can be determined in accord with engineering design considerations, as well as with regard to factors described herein, which affect selectivity, product removal and process efficiency. For discussion of design factors of suitable towers, reference is made to Chemical Engineers' Handbook, Perry (McGraw Hill Book Company), Section 14, Gas Absorption and Solvent Extraction, and Section 18, Liquied-Gas Systems.

The use of a contact reactor column provides a simple procedure for effecting the desired reaction in a contact reactor column, and quickly removing product. A stream containing butadiene reactant is passed through the column, reacting to some extent as it contacts the reaction medium, and with product being removed in the reactant stream to an extent depending upon conditions and flow rate. Butadiene and acetic acid are the essential reactants, along with metal oxidant. A 50% by weight solution of butadiene in acetic acid (prepared under pressure) can, for example, be used for instant admission of these reactants to the system. The acetic acid reactant, being less volatile than butadiene, can constitute a fair proportion of the liquid reaction medium in the column, with its proportion being determined by equilibrium between the reaction medium and the cycling stream. Some acetoxyhexenoic acids product may be entrained with reactant and removed with reactor overhead, as though line 12'; in FIG. 4. However, acetoxyhexenoic acids may accumulate in the reaction system and be removed periodically from reactor bottoms by purge line 17' in FIG. 4, and separated from high boiler or other materials similarly removed.

When a packed tower reactor is employed, the flow of materials through the packed tower will be adjusted to have good mass transfer and to avoid flooding. The tower and associated electrolysis cell can be sized for efficient operation together. The electrolysis cell will preferably have sufficient capacity, particularly anode area, to regenerate the metal oxidant at the rate utilized in the reactor. Conversely, it is desirable to operate the electrolysis cell at practical current densities, and for the reactor to provide sufficient metal ion for oxidation, in order to have good current efficiency. While the electrolysis cell as illustrated is in a container separate from the reactor, it is feasible to carry out the electrolysis in the reactor itself. Thus electrodes can be suspended in the packing material in the reactor. Alternatively, the electrodes can be suspended in a space in the reactor container above the packing material. The electrodes in the reactor can be used either with or without a divider. When a divider is used, it can conveniently be in the form of a cup of alundum or porous material around the cathode, leaving the anode exposed to the bulk of reacting materials, possibly as a cylinder of electrode material adjacent to the reactor wall. The current densities utilized for the present process can vary widely, but it may be desirable to operate in ranges from about 20 to about 100 or more milliamperes per cm. of nominal anode area, recognizing that the actual current densities may be lower if the true area of a high surface area anode is taken into consideration.

For further description of various operating considerations and materials and equipment for use in the present process, reference is made to the aforesaid U.S. Pat. No. 4,356,317.

EXAMPLE 10

A reaction system was utilized with a packed tower, reaction medium reservoir, electrolysis cell, and circulation pump. The tower was a glass cylinder, 5.08 cm. internal diameter, packed with 6 mm Berl saddles, 30 cm in height, with about 2.5 cm of 2 mm glass beads above the Berl saddle packing. The tower was jacketed for heating oil. The tower was joined by a conduit at its lower end to a 250 ml. flask serving as a reservoir. The flask was provided with an inlet near its top for butadiene, and an outlet at the bottom leading to a centrifugal micropump for circulating the reaction mixture to an electrolysis cell. The pump had zirconium metal in contact with the reaction mixture. A conduit was provided to conduct the reaction mixture to the top of the packed tower. A cooled-condenser was mounted on top of the tower to prevent substantial escape of volatile components other than butadiene. The electrolysis cell was a plate and frame cell of Ryton ® polyphenylene sulfide material and stainless steel with polytetrafluoroethylene fittings. The flow channel was 10 cm. long and tapered from 3.8 cm. wide at the center, with a total exposure of each electrode being about 28 cm². The anode was graphite felt, and the cathode a graphite plate, with approximately a 3 mm gap between the electrodes. The reservoir was heated with a heating mantle, and the pump and cell were heated by heating tape, all with temperature controls. To prepare a reaction medium, the following materials were used:

90 grams Mn(OAc)$_2$.4H$_2$O
90 grams LiOAc.2H$_2$O
120 grams KOAc
320 ml Ac$_2$O
200 ml acetic acid

(Ac represents CH$_3$C—)

The material was heated and stripped to a weight of 480 grams, and 470 grams was charged to the reaction system. Oil at 140° C. was circulated to the packed tower, and the pump and cell were heated at 135° C. Reaction was conducted with the reaction melt at 135° C., and butadiene circulating at 100 ml per minute. The reaction mixture was circulated at a speed to trickle through the packed tower, without flooding. The electrolysis cell was operated at 5.7 volts, with an amperage of 0.8. Samples were taken at intervals during an 8-hour run, and a final sample 1 hour later, with results as reported in Table 6.

TABLE 6

| Time Min. | % Current Efficiency | | | Lactone in Reaction Mix. (% by weight) |
| --- | --- | --- | --- | --- |
| | To lactone | To acetoxy hexenoic acids. | Total | |
| 285 | 39 | not detected | 39 | 0.6 |
| 375 | 37 | 4 | 41 | 0.9 |
| Final | 30 | not detected | 30 | 0.8 |

On the final sample, after addition of water to hydrolyze anhydride forms possibly present, analysis indicated 43% current efficiency to lactone, 5% to acetoxyhexenoic acids, and a lactone concentration of 1% by weight. It is probable that a hydrolysis procedure would also have improved results for the other samples, as the selectivity to desired products is generally expected to decline with increased reaction time and product concentration. The lactone referred to in the above results is γ-vinyl-γ-butyrolactone, and the acetoxyhexenoic acids are primarily a mixture of 6-acetoxy-4-hexenoic acid and 4-acetoxy-5-hexenoic acid.

EXAMPLE 11

A reaction was conducted as in Example 10, but with some acetic anhydride added to the electrolyte. A salt, acetic acid and acetic anhydride mixture as described in Example 10 was stripped to 480 grams, and 25 grams of acetic anhydride was added. A 350 gram amount of the resulting mixture was charged to the reaction system. Reaction was conducted with the reaction mixture at 132°–135° C. and cell voltage at 5.8 volts for 0.8 ampere. Butadiene flow rate was 100 ml/minute. Results are reported in Table 7.

TABLE 7

| Time (min.) | % Current Efficiency | | | Lactone in Reaction Mix. (% by weight) |
| --- | --- | --- | --- | --- |
| | To lactone | To acetoxy hexenoic acids | Total | |
| 150 | — | 33 | 33 | 0.4 (est.) |
| 240 | 10 | 26 | 36 | 0.5 (est.) |
| 330 | 15 | 24 | 39 | 0.7 (est.) |
| 435 | 7 | 25 | 32 | 0.7 (est.) |

After addition of water to the last sample, analysis indicated 9% current efficiency to lactone and 17% to acetoxyhexenoic acids.

EXAMPLE 12

A reaction was conducted as in Example 11, but with more acetic anhydride present. A salt and acetic mixture as in Example 11 was stripped to 455 grams, and 50 grams acetic anhydride was added. A 410 gram amount of the mixture was charged to the reaction system, and an additional 25 gram acetic acid was charged to the circulation pump for a total charge of 435 grams. An 8-hour reaction gave 5% current efficiency to the lactone, and 10% to acetoxyhexenoic acids.

EXAMPLE 13

The reaction system of Example 10 was modified to have a divided electrolysis cell through which the reaction mixture was cycled as anolyte. The cell had a separate circulation system for catholyte. A reaction medium was prepared as in Example 1, but containing a 0.46 gram amount of $Cu(OAc)_2.H_2O$. The mixture was stripped to 480 grams, and 300 grams was charged to the reaction system. The reaction was conducted with a butadiene flow of 100 ml/minute, reaction temperature of 133° C., and 5.9 volts ad 0.8 ampere current in the electrolysis cell. Samples were taken at intervals during the approximately 12-hour run. Results are reported in Table 8.

The divided electrolysis cell utilized above was constructed of Ryton ® polyphenylene sulfide resin frames used as electrode spacers and flow channels. The channels were 10 cm long, and 3.8 cm wide at the center, tapering to 1 cm wide at each end such that the total exposed area of each electrode was 28 cm². Each flow channel was 3 mm thick separated by a Nafion ®425 fluoropolymer resin ion exchange membrane such that the total cell gap was about 6 mm (The resin is a fluorinated hydrocarbon with pendant ether groups having sulfonic acid substituents). Two layers of Conwed ® XN1-2170 polyethylene mesh was placed in each flow channel to support the membrane, masking the electrodes to 16 cm² each.

As catholyte, a reaction medium similar to the anolyte can be used, but with manganese salts omitted as unnecessary. Thus 45 grams potassium acetate and 45 grams lithium acetate dihydrate can be admixed with 90 ml acetic anhydride and 100 ml acetic acid, stripped (with 40° C. and 15 mm Hg) to 175 grams and 168 grams charged as catholyte.

TABLE 8

| Time (min.) | % Current Efficiency | | | Lactone in Reaction Mix. (% by weight) |
|---|---|---|---|---|
| | To lactone | To acetoxy hexn. acids | Total | |
| 120 | 38 | 14 | 52 | 0.58 |
| 240 | 43 | 14 | 57 | 1.27 |
| 360 | 39 | 13 | 52 | 1.77 |
| 480 | 33 | 12 | 45 | 2.01 |
| 600 | 30 | 11 | 41 | 2.30 |
| 710 | 26 | 11 | 37 | 2.40 |

EXAMPLE 14

A reaction was conducted as in Example 13, but employing a larger amount of copper salt, 0.92 grams. The final current efficiency was 13% to lactone and 6% to acetoxyhexenoic acids. Acetoxyacetic acid was also produced, at a current efficiency of 7%. Gas analysis indicated 96% butadiene and 2.3% carbon dioxide. Such production of carbon dioxide, presumably by a Kolbe reaction, generally indicates poor efficiency of the desired electrolysis because of electrode fouling. It was recognized that the circulation rate through the electrolysis cell was slower than desirable, in this example as well as in other examples. The capacity of the contact tower can be increased to permit more rapid circulation of reaction medium for better results, or other changes can be made to adjust the relative capacities of the packed tower and electrolysis cell.

EXAMPLE 15

A reaction medium was prepared as in Example 10, with stripping to leave approximately 40 weight percent acetic acid. As in other preparations, the acetic anhydride initially included was intended to take up water of hydration from the salt hydrates. To 1328 grams of a so-prepared mixture, 75 grams acetic anhydride was added as excess, along with 1.2 grams $Cu(OAc)_2.H_2O$ and the mixture heated to liquification. A 306 gram amount was charged as anolyte to the reaction system described in Example 13. The reaction was run at a butadiene flow rate of 100 ml/minute with the reaction medium at 131° C. Cell voltage was 6 volts, and the current was 0.8 ampere. The reaction was conducted for 8.5 hours, with the current being shut off at 8 hours. Results are reported in Table 9.

TABLE 9

| Time (min.) | % Current Efficiency | | | Lactone in Reaction Mix. (% by weight) |
|---|---|---|---|---|
| | To Lactone | To acetoxy Hexen. acids | Total | |
| 110 | — | 13 | 13 | 0.13 |
| 240 | 6 | 12 | 18 | 0.41 |
| 360 | 6 | 12 | 18 | 0.60 |
| 510 | 4 | 11 | 15 | 0.67 |

Gas analysis showed 98% butadiene and 2.1% carbon dioxide.

It is to be recognized that in the illustrated procedures herein with a contact tower, conditions have not been optimized. Thus various reaction temperatures, reaction medium flow rates, and tower sizes and capacities have not been investigated. Also from $CO_2$ production there was an indication of electrode fouling. When the procedure of Example 13 was repeated, but without the packed tower in the system, the results were poorer, with 24% current efficiency to the lactone and 3% to acetoxyacids at 135 minutes, and 17% and 3% respectively at 405 minutes. However, a repetition of Example 15 but without the tower gave better results. From results in both runs, it was suspected that the anode had become fouled (sometime in the conduct of the above examples), and it was replaced with a new anode. A repetition of the comparison run without the packed tower, then gave much better results, with initial current efficiencies (corrected for membrane transport of potassium ion and acetic acid) to total desired product in this and subsequent procedures approaching 90%. Also, the $CO_2$ in the gas was now much lower, being 0.15% compared to a nominal 101% butadiene in the gas analysis for the foregoing described procedure.

In the above illustrated procedures with a contact tower, provisions were not made to determine the amount of γ-vinyl-γ-butyrolactone removed from the contact tower with the butadiene stream. Instead, a condenser was employed to return product and moderately volatile material to the reaction. While the resulting demonstration of the reaction with the contact tower does not include product removal, it has been determined that a butadiene and acetic acid stream can remove γ-vinyl-γ-butyrolactonne from a liquid salt medium, as described hereinabove. Additionally, it has been demonstrated herein, that such a stream can remove γ-vinyl-γ-butyrolactone from such a liquid salt medium during a reaction to form it from butadiene and acetic acid, with approximately half of the lactone product in one procedure being found in product condensate from a distillation condenser connected to the reactor, rather than in the reactor. Similar results can be obtained in a packed tower system by equipping it with a distillation condenser connected to the top of the packed tower, to condense and isolate the product stream. Tower height, reaction temperature and flow rates can be adjusted for continuous removal of a suitable portion of the product at preferred selectivities.

We claim:

1. The process of preparing γ-vinyl-γ-butyrolactone which comprises reacting butadiene and acetic acid in the presence of a metal salt oxidant in a molten salt medium containing salts having melt properties to make the medium liquid under reaction conditions with manganese salts employed as oxidant comprising about 10% to 50% of the salts and acetic acid comprising about 20% to about 50% by weight of the molten salt medium at temperatures in the range of 130° C. to 180° C.

2. The process of claim 1 in which butadiene and acetic acid are brought into contact with a molten salt medium and γ-vinyl-γ-butyrolactone is removed from such medium by sparging with butadiene reactant.

3. The process of claim 1 in which the metal salt oxidant is regenerated by electrolysis at an anode in contact with the molten salt medium.

4. The process of claim 1 in which the molten salt medium is cycled from a reactor to an electrolysis cell for regeneration of trivalent manganese.

5. The process of claim 1 in which the reaction temperature is in the range of about 130° to about 150° C.

6. The process of claim 1 in which the salt medium contains a small amount of copper salts and a small amount of acetic anhydride.

7. The process of claim 1 in which the process is carried out on a continuous basis and the concentration of γ-vinyl-γ-butyrolactone product in the salt medium is kept below 10% by weight.

8. The process of claim 1 in which removal of γ-vinyl-γ-butyrolactone product is effected on a continuous basis by entrainment with a reactant stream.

9. The process of claim 1 in which the molten salts include alkali metal salts along with manganese salts.

10. The process of claim 9 in which the salts include a substantial amount of lithium acetate to lower the melting point thereof.

11. The process of claim 9 in which lithium and potassium acetates are present in the salts in a ratio between about 1:1 and about 1:7 lithium to potassium on a mole basis.

12. The process of claim 1 in which the salt medium is such as to be a low viscosity liquid at the reaction temperature utilized.

13. The process of claim 9 in which 25 to 35% by weight of the salts in the salt medium is manganese acetate and lithium acetate is in slight molar excess over other alkali metal acetate.

14. The process of claim 1 in which reaction is effected in a reactor with high surface to volume ratio, being a type of column used for absorption, stripping, desorption or distillation and characterized as a plate or packed column.

15. The process of claim 1 in which quaternary ammonium salts are present.

16. The process of claim 1 in which quaternary ammonium acetate is employed.

17. The process of preparing γ-vinyl-γ-butyrolactone which comprises reacting butadiene and acetic acid with metal salt oxidant at elevated temperature in a reactor with high surface to volume ratio, being a type of column used for absorption, stripping, desorption, or distillation and characterized as a plate or packed column, with the reaction medium used containing salt electrolytes and manganese salt as the metal salt oxidant constituting 10% to 50% by weight of the salts and acetic acid constituting about 20% to about 50% of reaction medium, at temperatures in the range of 130° to 180° C.

18. The process of claim 17 in which the reactor is adapted for mass transfer between gas and liquid phases.

19. The process of claim 17 in which the reactor is a packed tower suitable for use as an absorption tower.

20. The process of claim 19 in which the metal salt oxidant is a manganese salt and a liquid reaction medium is used containing salt electrolytes and the metal salt oxidant is is regenerated electrolytically during the process.

21. The process of claim 20 in which alkali metal acetates including lithium acetates along with other alkali metal acetates are utilized.

22. The process of claim 20 in which liquid reaction medium flows downward through the packed tower and counter current to butadiene flowing upward through the tower.

23. The process of claim 22 in which butadiene is recycled through the tower with provision for condensation and removal of γ-vinyl-γ-butyrolactone product before return of butadiene to the tower.

24. The process of claim 22 in which reaction medium containing manganese is cycled through an electrolysis cell for oxidation of manganese for further use in the process.

25. The process of claim 24 in which the reactor is operated at temperature sufficiently high to favor production of γ-vinyl-γ-butyrolactone at the expense of acetoxyhexenoic acids.

26. The process of claim 24 in which acetic anhydride is included in the reaction medium.

27. The process of claim 26 in which a copper salt is included in the reaction medium.

* * * * *